US00PP23495P2

(12) United States Plant Patent
Kordes

(10) Patent No.: US PP23,495 P2
(45) Date of Patent: Mar. 26, 2013

(54) HYBRID TEA ROSE PLANT NAMED 'KORPAUVIO'

(50) Latin Name: *Rosa hybrida*
Varietal Denomination: KORpauvio

(75) Inventor: Wilhelm Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 888 days.

(21) Appl. No.: 12/228,865

(22) Filed: Aug. 15, 2008

(51) Int. Cl.
*A01H 5/00* (2006.01)

(52) U.S. Cl. ..... Plt./118
(58) Field of Classification Search ..... Plt./118
See application file for complete search history.

(56) References Cited

PUBLICATIONS

2007/1335, European Union CVPO summary, Jun. 13, 2007, European Union.

*Primary Examiner* — Annette H Para

(57) ABSTRACT

A new and distinct variety of rose with long lasting, novel medium pink flowers, and attractive foliage with moderate disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

CROSS REFERENCES AND FEDERAL R&D STATEMENT

There are no cross referenced or related applications. This variety was developed without the aid of any research grant.

Latin name of GENUS and SPECIES

The botanical classification of the new rose plant is *Rosa hybrida.*

Variety Denomination

The denomination of the new variety is 'KORpauvio'.

BACKGROUND OF THE INVENTION

The new variety of rose plant of the present invention originated from a controlled crossing in a breeding program of two distinct parents during the summer of 1999. The crossing was between 'MEIzeli' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpauvio'.

SUMMARY OF THE INVENTION

The new rose plant may be distinguished from its seed parent, 'MEIzeli', by the following combination of characteristics:

1. The flower color of 'MEIzeli' is light pink, while the flower color of 'KORpauvio' is medium pink.
2. The petal count of 'MEIzeli' is double, while the petal count of 'KORpauvio' is very double.

The new rose plant may be distinguished from its pollen parent, an 'un-named seedling' by the following combination of characteristics:

1. The flower color of the 'un-named seedling' is cream pink, while the flower color of 'KORpauvio' is medium pink.
2. The height of the 'un-named seedling' is 100-150cm, while the height of 'KORpauvio' is 80-100cm.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars. These objectives have been substantially achieved and in that distinguish 'KORpauvio' from all other varieties of which we are aware.

As part of a rose development program, Wilhelm Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpauvio' was selected in May, 2000 from the seedling beds to be asexually propagated for further evaluation. The first asexual propagation of 'KORpauvio' was done by budding to seedling understocks in July, 2000 at the inventor's nursery in Offenseth-Sparrieshoop, Germany.

This initial and other subsequent propagations conducted in controlled environments demonstrate that 'KORpauvio' reproduces true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'KORpauvio'. Specifically illustrated in SHEET ONE is stem exhibiting thorns; tight bud, ¼ opened flower bloom and bloom; juvenile foliage and tip of stem; dissected receptacle and detached sepal; and leaves.

DETAILED BOTANICAL DESCRIPTION

The following is a description of 'KORpauvio', as observed in its growth in July, 2008 in a nursery in Jackson County, Oreg. on plants of three years of age. Color references are made using The Royal Horticultural Society (London, England) Colour Chart, 2001 except where common terms of color are used.

For a comparison, several physical characteristics of the rose variety 'KORaburg', a rose variety from the same inventor described and illustrated in U.S. Plant patent application No. 17,763 and issued on May 29, 2007 are compared to 'KORpauvio' in Chart 1:

CHART 1

| | 'KORlutmag' | 'KORdwarul' |
|---|---|---|
| Petal count | Double petaled flower with an average of 28-32 petals. | Single petaled flower with an average of 7 petals. |
| Petal color, ¼ open bloom | Upper surface: Yellow Group 13C. Lower surface: Yellow Group 10A with intonations on outer petal margins of Red Group 51A and Red Group 51B. | Upper surface: Red-Purple Group 60A. Lower surface: Red-Purple Group 60B. |

Parents:

*Seed Parent.*—'MEIzeli'.

*Pollen Parent.*—an 'un-named seedling'.

Classification:

*Botanical classification.*—*Rosa hybrida,* 'KORpauvio'.

*Commercial classification.*—Hybrid Tea rose.

FLOWER AND FLOWER BUD

Blooming habit: Recurrent.

Flower bud:

*Size.*—Upon opening, 40-45 mm in length from base of receptacle to end of bud and 25-30 mm in diameter at its widest point.

*Bud form.*—Short and globular.

*Bud color.*—As sepals first unfold, bud color is Red-Purple Group 58A and Red-Purple Group 58D. When ¼ open, the upper surface of petals is Red-Purple Group 58B (marginal zone) and Red Purple Group 62C (middle zone). The lower surface of petals is Red-Purple Group 58B (marginal zone) and Red-Purple Group 62B (middle zone).

*Sepals.*—Size: Average 30 -35 mm long×12 -14 mm wide. Shape: Sepals generally subulate. Sepal apex is generally cirrose. Strong foliaceous appendages on three of the five sepals. Base is flat at union with receptacle. Quantity: Five. Margins: With stipitate glands on inner surface. Surface texture: Inner side: Covered in long, fine, white hairs and stipitate glands. Outer surface:Smooth. Color: Upper surface Green Group 138B. Lower surface Yellow-Green Group 144A. Intonations: Greyed-Red Group 182B.

Receptacle:

*Surface.*—Smooth

*Color.*—Yellow-Green Group 144A. .

*Shape.*—Funnel-shaped.

*Size.*—7 -8 mm (h)×14 -15 mm (w).

Peduncle:

*Surface.*—With stipitate glands and fine white hairs.

*Length.*—60-70 mm average length.

*Diameter.*—4-5 mm average diameter.

*Color.*—Yellow-Green Group 144A.

*Strength.*—Somewhat strong.

*Borne.*—Singly. 1-3 buds per flowering stem.

*Anthocyanin.*—Greyed-Red Group 181A.

Flower bloom:

*Fragrance.*—Strong.

*Duration.*—Long lasting. The blooms have a duration on the plant of approximately 6 to 7 days. Senesced petals drop away cleanly.

*Size.*—Large flowered garden rose. When open, the average flower diameter is 90 -100 mm and the average flower height is 50 -55 mm.

*Form.*—Shape of flower when viewed from the side: Upon opening, upper part: Flattened convex. Upon opening, lower part: Concave. Open flower, upper part: Flattened convex. Open flower, lower part: Concave.

Color:

*Upon opening, petals.*—Outermost petals: Outer Side: Marginal zone: Red-Purple Group 58B. Middle zone: Red-Purple Group 62C. Inner Side: Marginal zone: Red-Purple Group 58B. Middle zone: Red-Purple Group 62B and Red-Purple Group 62C. Innermost petals: Outer Side: Marginal zone: Red-Purple Group N57A. Middle zone: Red-Purple Group 62D. Inner Side: Marginal zone: Red-Purple Group 58B. Middle zone: Red-Purple Group 62D.

*Upon opening, basal petal spots.*—Basal petal spot, outermost petals: Outer Side: Green-Yellow Group 1D. Inner Side: Green-Yellow Group 1A. Basal petal spot, innermost petals: Outer Side: Green-Yellow Group 1A. Inner Side: Yellow Group 2A.

*After opening, petals.*—Outermost petals: Outer Side: Red-Purple Group 58B and Red-Purple Group 58C. Inner Side: Marginal zone: Red-Purple Group 58C. Middle zone: Red-Purple Group 62C. Innermost petals: Outer Side: Red-Purple Group 62C. Inner Side: Red-Purple Group 62D.

*After opening, basal petal spots.*—Basal petal spot, outermost petals: Outer Side: Green-Yellow Group 1D. Inner Side: Green-Yellow Group 1C. Basal petal spot, innermost petals: Outer Side: Green-Yellow Group 1D. Inner Side: Green-Yellow Group 1D. Variegations: None.

General Tonality: On open flower Red-Purple Group 58B (margins) and Red-Purple Group 62B (middle). No change in the general tonality at the end of the 6th day. Afterwards, general tonality is Red-Purple Group 62C and Red-Purple Group 62D.

Petals:

*Petal count.*—Approximately 50-55 petals under normal conditions.

*Petal Reflex.*—Petals reflex strongly.

*Petal Edge.*—Entire and slightly ruffled.

*Petal Shape.*—Round. Apex shape is round. Shape of base is round.

*Petal Size.*—50 mm long; 50 mm wide.

*Thickness.*—Thick.

*Petal Arrangement.*—Generally in a regular pattern with overlapping edges.

Petaloids: Present.

*Petaloid count.*—Average of 4-6 per flower.

*Petaloid Edge.*—Undulated and indented.

*Petaloid Texture.*—Ruffled.

*Petaloid Shape.*—Elongated. Entire. Shape of apex is round, shape of base is pointed.

*Petaloid Size.*—Petaloids are 20-25 mm long and 20 mm wide.

*Petaloid Color.*—Color of inner side is Red-Purple Group N57B. Color of outer side is Red-Purple Group N57A.

Reproductive Organs:

*Pistils.*—Approximately 70-80 present. Stigmas: Location: Slightly inferior in position to anthers. Color: Green-Yellow Group 1D. Styles: Length: 7-8 mm long. Color: Green-White Group 157D. Intonations of Red Group 51B.

*Stamens.*—Approximately 70-80 on average and regularly arranged. Anthers: Size: 3-4 mm long. Color: Yellow Group 13A and Yellow Group 13C. Pollen: Absent. Filaments: Color: Red Group 47B. Length: 7-8 mm.

THE PLANT

*Plant growth.*—Vigorous. Upright to bushy habit. When grown as a budded nursery plant the average plant height is 80-100 cm and the average plant width is 60-80 cm.

*Stems.*—Stem color: Young wood: Green Group 138A. Older wood: Green Group 137B. Stem surface: Young wood: Smooth. Older wood: Rough.

*Prickles.*—Present. Incidence: 6-12 per 10 cm of stem. Size: Average length: 6 mm. Color: Immature prickles: Greyed-Yellow Group 160A. Mature prickles: Greyed-Orange Group 165B. Senescing to Greyed-Orange Group 165A. Shape: Concave. Anthocyanin: Color: Greyed-Red Group 178B.

*Leaves and leaflets.*—Normally 5-7 leaflets on normal leaves in middle of the stem. Venation pattern: Pyramidal net pattern. Leaf size: 140-150 mm (l)×100-120 mm (w). Quantity: Very. Texture: Upper side of leaflet: Semi-glossy and smooth. Under side of leaflet: Matte and rough. Color, mature foliage: Upper Leaf Surface: Green Group 137A. Lower Leaf Surface: Yellow-Green Group 147B. Color, juvenile foliage: Upper Leaf Surface: Green Group 137A. Lower Leaf Surface: Yellow-Green Group 147B. Anthocyanin intonation: Greyed-Red Group 182A.

*Stipules.*—Size: 20-25 mm long. 6 mm between the tips of the stipule. Main body of stipule 8 mm in width. Shape: Longitudinally flanged or winged along middle. Apex: pointed. Base: rounded. Stipule color: Green Group 138A. Presence of stipitate glands: Present on margins. Margins: Serrated. With stipitate glands and fine white hairs.

*Petiole.*—Length: 15-20 mm. Diameter: 1-2 mm. Petiole color: Green Group 138A. Underneath: An occasional prickle. Stipitate glands: Present on margins. Margins: With long white hairs and stipitate glands. Anthocyanin: Greyed-Red Group 182A.

*Petiole Rachis.*—Length: 20-25 mm. Diameter: 1-2 mm. Color: Green Group 138A. Margins: With long white hairs and stipitate glands. Prickles: An occasional prickle underneath. Stipitate glands: Present on margins. Anthocyanin: Greyed-Red Group 182A.

*Leaflets.*—Size: Average size of the terminal leaflet is 60 mm (l)×70 mm (w). Shape: Broadly ovate. Base: Ovate. Apex: Acute Margins: Serrated. Texture: Thick and leathery.

Hips/Seed formation: None observed.

Winter hardiness: To date, the variety has been grown successfully in Zone 5.

Disease resistance: Above average resistance to rust and Black spot diseases under normal growing conditions.

I claim:

1. A new and distinct variety of rose plant characterized by the following combination of characteristics:

(a) Forms attractive, long lasting medium pink flowers;

(b) Exhibits upright to bushy growth habit;

(c) Propagates well using traditional methods, and;

(d) Exhibits resistance to disease under normal growing conditions, substantially as herein illustrated and described.

* * * * *

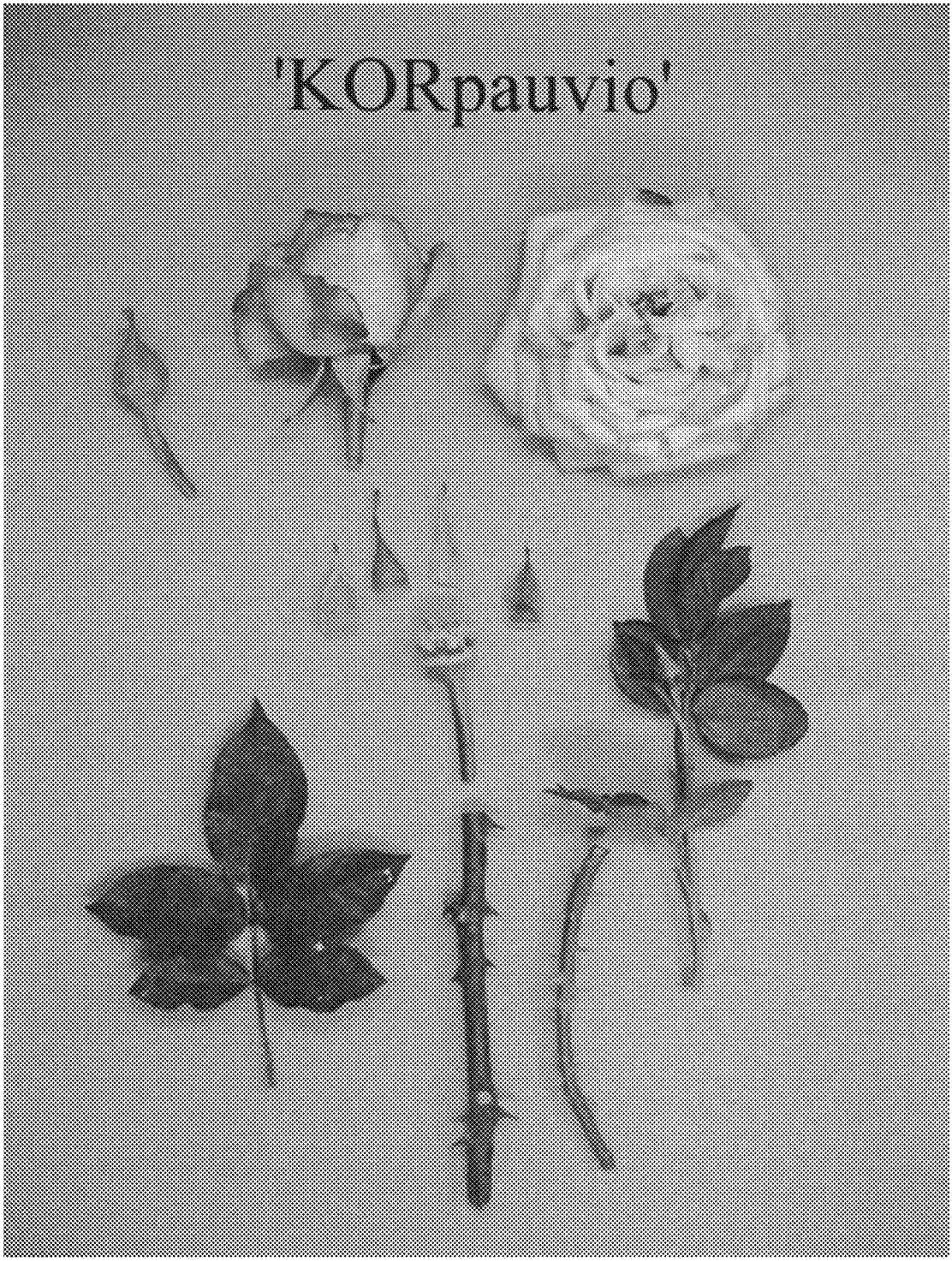
'KORpauvio'